United States Patent [19]
McKeique

[11] Patent Number: 5,255,555
[45] Date of Patent: Oct. 26, 1993

[54] METHOD FOR DETERMINING PARTICLE RESPONSE CHARACTERISTICS

[75] Inventor: Kevin McKeique, New York, N.Y.

[73] Assignee: The BOC Group, Inc., New Providence, N.J.

[21] Appl. No.: 874,465

[22] Filed: Apr. 27, 1992

[51] Int. Cl.$^5$ .................................... G01D 21/00
[52] U.S. Cl. ................................. 73/28.01; 73/865.9
[58] Field of Search ............... 73/1 R, 1 G, 28.01, 73/865.9, 38; 437/8

Primary Examiner—Hezron E. Williams
Assistant Examiner—Michael Brock
Attorney, Agent, or Firm—David M. Rosenblum; Larry R. Cassett

[57] ABSTRACT

The present invention provides a method and apparatus for determining the particle response characteristic of a device. In accordance with the apparatus and the method, a fluid which can comprise a gas stream is passed through the device and an input pulse of particles is introduced into the fluid before entering the device. As a result, an output pulse of particles is produced in the fluid being discharged from the device. The input and output pulses of particles are recorded on the basis of particle count versus time. A sufficient number of repetitions are completed such that signal averaging of the input and output pulses of the particles produces statistically repeatable reference and response pulses of particles. A comparison between the reference and response pulses of particles is the particle response characteristic of the device.

11 Claims, 7 Drawing Sheets

METHOD FOR DETERMINING PARTICLE RESPONSE CHARACTERISTICS

BACKGROUND OF THE INVENTION

The present invention relates to a method and apparatus for determining a particle response characteristic of a device in order to model the degree to which contaminants present within a fluid passing through the device will be delayed or retained within the device. More particularly, the present invention relates to such a method and apparatus in which pulses of particles are introduced into a fluid before the fluid passes into the device to derive statistically repeatable reference and response pulses which form the particle response characteristic of the device.

Ultra-high purity gases pass through much of the equipment, for example, process piping, valves, flow meters, rapid thermal processors and etc. used in the manufacture of semiconductors. Prior to use, the equipment is purged with an ultra-high purity gas to eliminate possible contaminants. For instance, during the loading of wafers into a process chamber of a rapid thermal processor, the process chamber is exposed to ambient air. Air, however, contains moisture which is an undesirable contaminant in the semiconductor manufacturing process. Therefore, the process chamber is purged with an inert stream of gas, generally composed of ultra-high purity nitrogen. In order to insure that the wafers will be processed in a moisture-free environment, the dry down characteristics of the process chamber are measured with a moisture analyzer to determine the length of time required to purge the process chamber so that a sufficiently low level of moisture will exist within the process chamber.

During the purging, the manufacturing process is at a standstill and thus, it is important to minimize the time spent in purging such equipment. As far as is known by the inventor herein, there is no test apparatus or method that can be used to select or design equipment so that the equipment will have the lowest possible retention of contaminants and thus, have the lowest purge time. Another problem relates to the sampling of the purge gas to insure that no contaminants are present in the equipment of interest. For instance, during the determination of the drydown characteristics of a rapid thermal processor many independent observations are made of the moisture content of the purge gas flowing from the process chamber. However, there is no known way to insure that observations are being made that take into account the time resolution capability of the sampling system; in other words, the degree to which piping and equipment used in connection with the sampling system are retaining contaminants such as moisture.

As will be discussed, the present invention provides a method and apparatus for modeling the degree to which a particular device will retain fluid borne contaminants by determining a particle response characteristic of the device.

Summary of the Invention

The present invention provides a method of determining a particle response characteristic of the device. In accordance with a step (a) of the method, an input pulse of particles is introduced into a flowing fluid. Thereafter, the flowing fluid is introduced into the device (step (b)), after the introduction of the input pulse of particles, so that an output pulse of particles is present in the fluid after the fluid has passed through the device. In accordance with steps (c), (d), (e) and (f), input and output counts of particles produced by the input and output pulses of particles, respectively, on a particle count versus time basis, are measured and recorded. In accordance with a step (g) of the method, steps (a), (b), (c), (d), (e) and (f) are repeated such that a sufficient number of input and output counts of particles are produced that signal averaging of the input and output counts of particles produces statistically repeatable reference and response counts of particles, respectively, on the particle count versus time basis. Input and response counts of particles are determined in accordance with a step (e) of the method from the recorded input and output counts of particles by signal averaging the input and output counts of particles. A comparison between the reference and response counts of particles is the particle response characteristic of the device.

In another aspect, the present provides an apparatus suitable for use in determining a particle response characteristic of a device. The apparatus comprises a fluid means for creating a fluid. An input pulse introduction means is provided for repeatedly generating and introducing input pulses of particles into the flowing fluid before the flowing fluid passes into the device. The input pulse introduction means is adapted to be connected to the device such that output pulses of the particles are present in the flowing fluid after the flowing fluid is passed through the device. The input pulse introduction means is adapted to repeatedly generate input pulses of the particles and, therefore, the output pulses of the particles such that a sufficient number of input and output counts of particles, on a particle versus time bases, are produced from the input and output pulses of particles, respectively, that signal averaging of the input and output counts of the particles produces statistically repeatable reference and response counts of particles, respectively, again, on the particle count versus time basis. A recording means is provided for recording the input and output counts of particles. The signal averaging of the input and output counts of the particles determines the reference and response counts of particles. A comparison between the reference and response counts of particles is the particle response characteristic of the device.

As mentioned previously, the comparison between the reference and response counts of particles is the particle response characteristic device. The particle response characteristic of a device is a model of the degree to which contaminants present within a fluid being passed through a device will be delayed or retained within the device. For instance, the time lag between the reference and response counts is indicative of the effective volume of the device. The effective volume in the present context is the volume of the device which the fluid traverses as it passes through the device. The effective volume may differ from the geometrical volume of the device as a result of the flow pattern of the fluid through the device. This aspect of the particle response characteristic of a device can be used to select devices that have a minimum effective volume and therefore, presumably retain the least amount of contaminants. In addition, the time lag is useful for synchronization of analytical and process equipment. For example, sampling systems consisting of tubing, fittings, valves and gauges are typically used to connect process equipment with analytical instrumentation. The time required for the fluid to pass through the sampling system must be known if the detected quantity is to be related to events occurring in the particular piece of process equipment. The particle response characteristic provides a precise means for establishing synchronization. Another aspect is a comparison that involves taking a difference between the half height widths of the reference and response count curves (plotted curves of particle count versus time). This difference indicates the time resolution that is possible in the device. For instance, changes in particle counts which occur at time intervals that are less than the time resolution cannot be observed. This feature can be used to select appropriate time intervals for sampling contaminants present in a fluid being discharged from a device to assure that the count of the sampled contaminants reflect the state of the fluid as discharged from the device. If particular sampling time intervals are required, sampling systems can be designed and selected that will allow sampling to take place within such sampling time intervals.

BRIEF DESCRIPTION OF THE DRAWINGS

While the specification concludes with claims particularly pointing out and distinctly claiming the subject matter that Applicant regards as his invention is believed that the invention will be better understood when taken in connection with the accompanying drawings in which:

DETAILED DESCRIPTION

Figure 1:
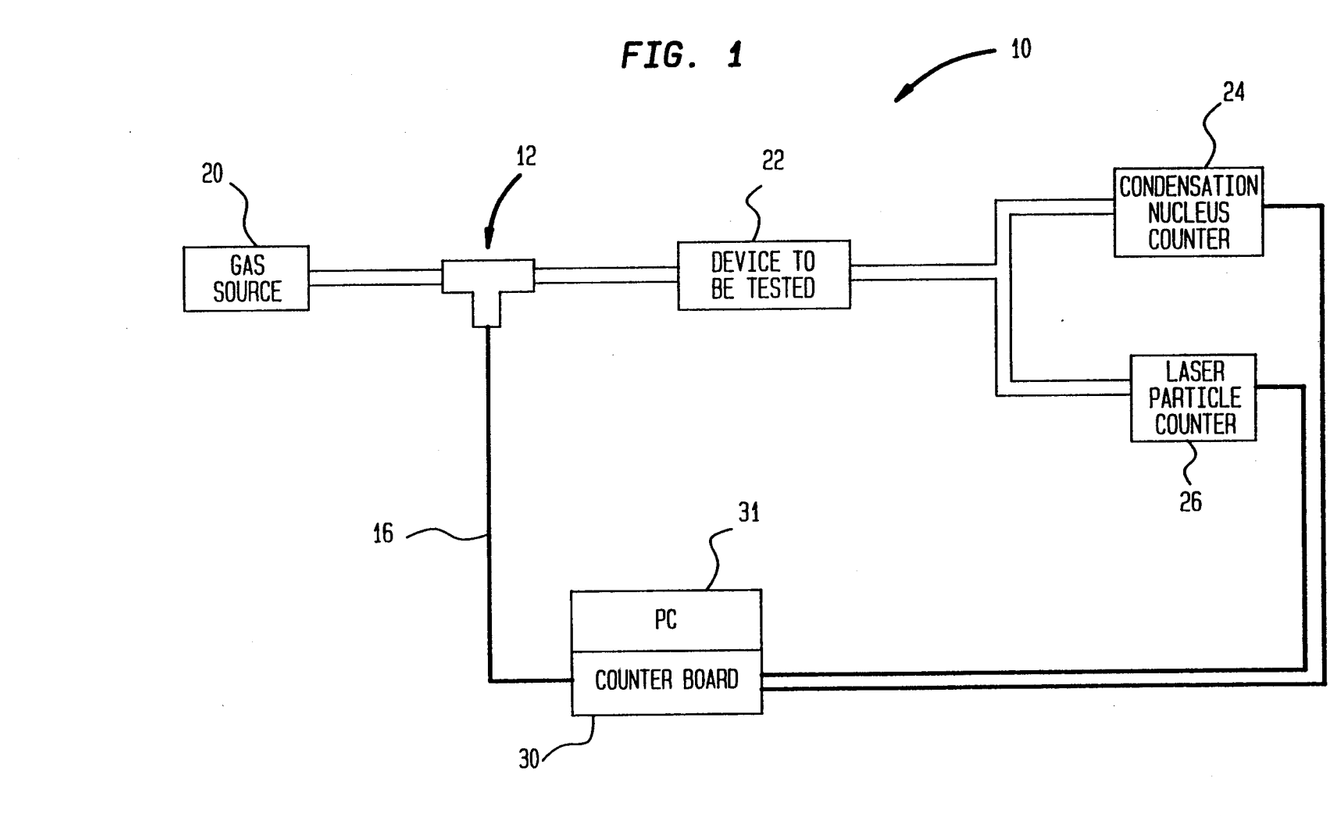
FIG. 1 is a schematic view of an apparatus in accordance with the present invention.

With reference to FIG. 1, an apparatus 10 is illustrated in accordance with the present invention for use in determining a particle response characteristic of a device, such as a valve, rotameter, sampling tube, or other equipment used in connection with the distribution or use of an ultra-high purity gas. In this regard, while the present invention has particular application to devices involved in ultra-high purity gas distribution and uses, it also has general applicability to devices in which any type of fluid passes through the device during the use of the device.

Figure 2:
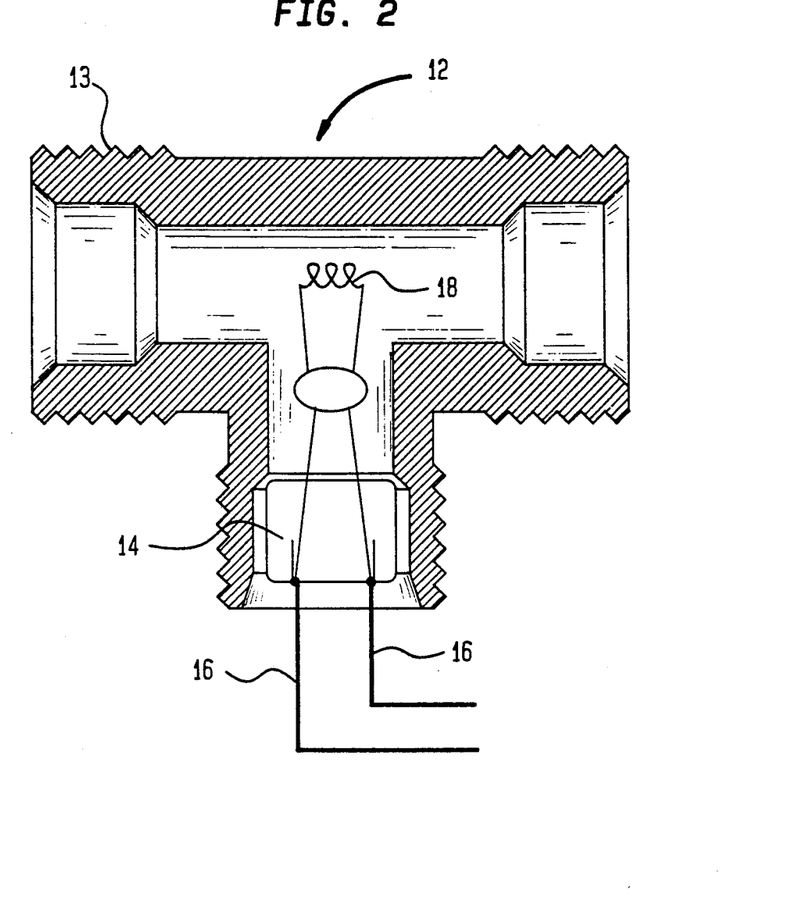
FIG. 2 is a sectional view of a particle generator in accordance with the present invention.

With additional reference to FIG. 2, apparatus 10 includes a particle generator 12 that is specifically designed to introduce particles into a gas stream to be passed through a device. Particle generator 12 consists of a housing 13 that can be formed of a T-like fitting having three legs. In one leg, a feed through 14 is provided for supporting a filament 18 within the T-like fitting. When electrical power is applied to leads 16, filament 18 is raised to a high enough temperature to effect a reaction between the filament 18 and the gas surrounding filament 18. If during the application of electrical power, a gas such as nitrogen is passed through the the other two inline legs of the T-like fitting, particles will be created that substantially comprise nitrides of Tungsten such as $WN_4$. The amount of particles that is created is dependent upon the power applied through filament 18 and the duration of time that the power is applied. As can be appreciated, other gases and filaments other than tungsten can be used which will produce discrete particles when an electrical current is passed through a filament. In this regard oxygen can be used to create particles formed of oxides of Tungsten such as $WO_3$ or $W_4O_4$ or mixtures of nitrogen and oxygen can be used in any proportion with or without the presence of additional components, for instance air.

Particle generator 12 is illustrated as being connected between a gas source 20 and a device 22 along the two inline legs of the T-like fitting forming housing 13 thereof. Particles produced by particle generator 12 will be introduced into the gas stream and will enter device 22 through entrainment within gas flowing from gas source 20 into particle generator 12. The input pulse of particles will produce an output pulse in response to such input pulse after the gas passes through device 22. The output pulses are sensed or measured by either a condensation nucleus counter 24 or a laser particle counter 26. At very high particle counts, the condensation nucleus counter will be overwhelmed, and at very low particle counts, the laser particle counter will be ineffective to sense the particles. Hence, the use of two particle counters ensures that particles will be counted over a range that encompasses both high and very low particle counts.

Figure 3:
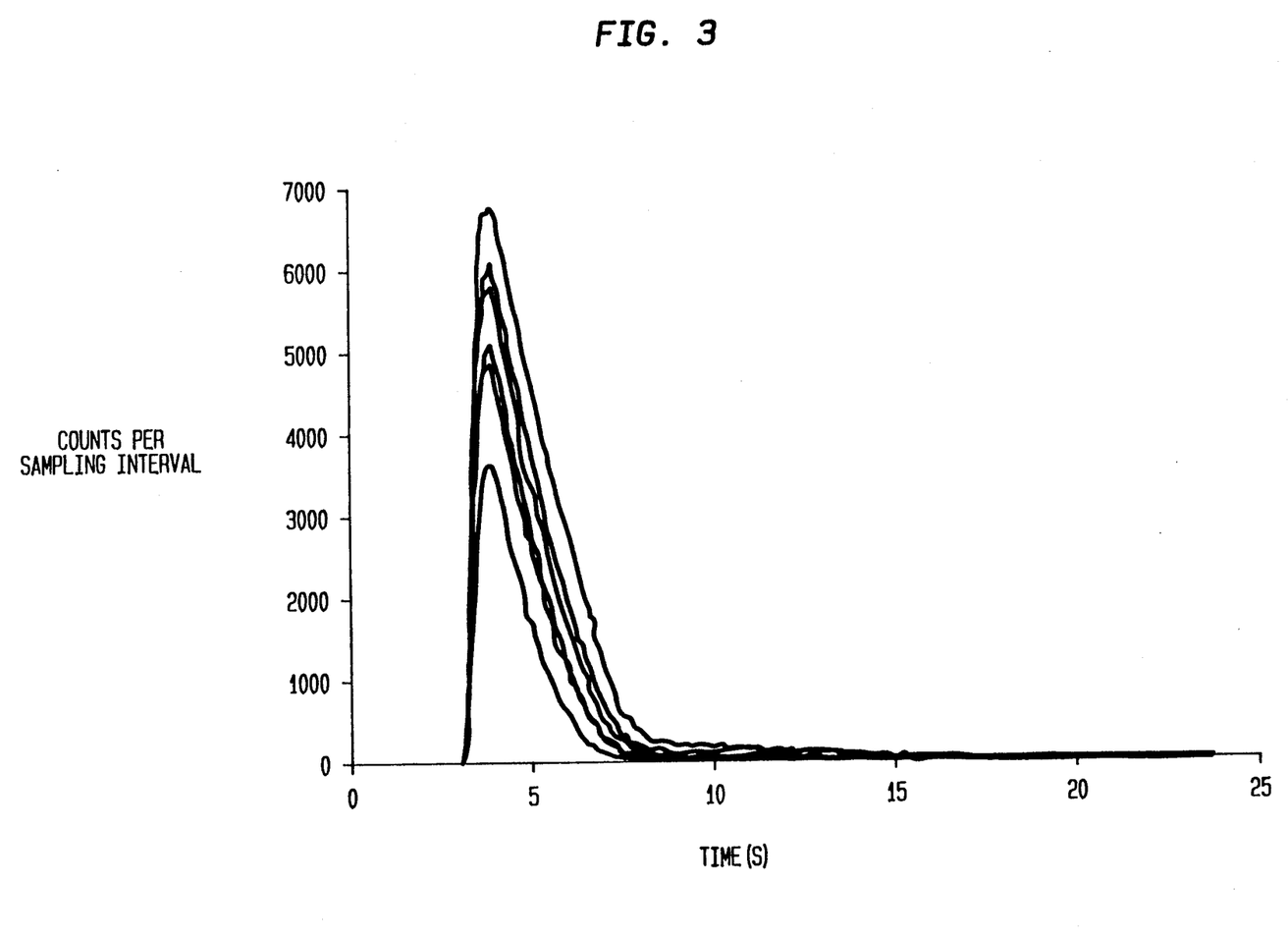
FIG. 3 is a plot of recorded input counts of particles to be signal averaged for use in determining a reference pulse.

With reference to FIG. 3, it can be seen that even if power is applied to particle generator 12 for an equal number of times a slightly different curve shape is observed. By the same token, output pulses in response to the input pulses will lag and have different curve shapes even when equal power is applied for equal time intervals. Therefore, in order to provide meaningful results which are indicative of response and can serve as a basis of comparison, the input counts of particles are signal averaged to produce a reference count of particles, and the output of counts of particles are then signal averaged to produce a response count of particles. The number of repetitions of input and output count measurements is a number that is determined to be that which will yield statistically repeatable reference and response pulses. That is, if for instance, 10 input and output pulses are produced and particle counts recorded and then signal averaged, the reference and response pulses will remain essentially unchanged no matter how many different times the experiment is carried out.

In apparatus 10, input and output counts of particles cannot be simultaneously measured by particle counters 24 and 26 because the sensing of the input counts would remove particles from the gas stream and thus effect the shape of the output counts. Therefore, a series of input counts of particles are produced and recorded for a statistically repeatable number of times with particle generator 12 connected directly to the particle counters (24 and 26). Thereafter, the input pulses of particles are produced again for the same number of time but with particle generator 10 connected to device 22 and with the particle counters measuring the output counts of the particles which are also recorded. The input and output counts of particles are then signal averaged to produce the reference and response counts of particles. The reference and response counts of particles are plotted for visual comparison.

Figure 4:
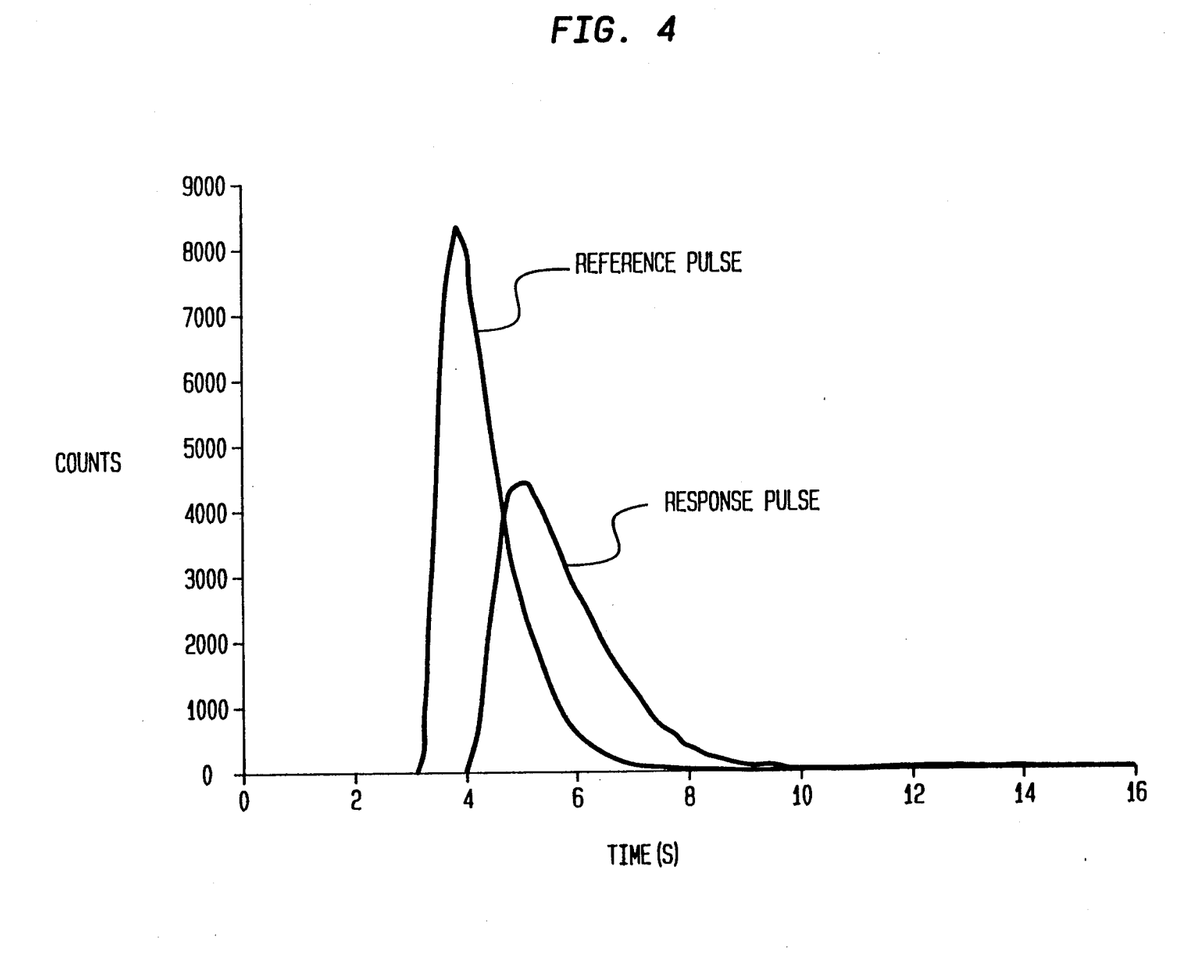
FIG. 4 is a plot of the particle response characteristic of a sampling tube.
Figure 5:
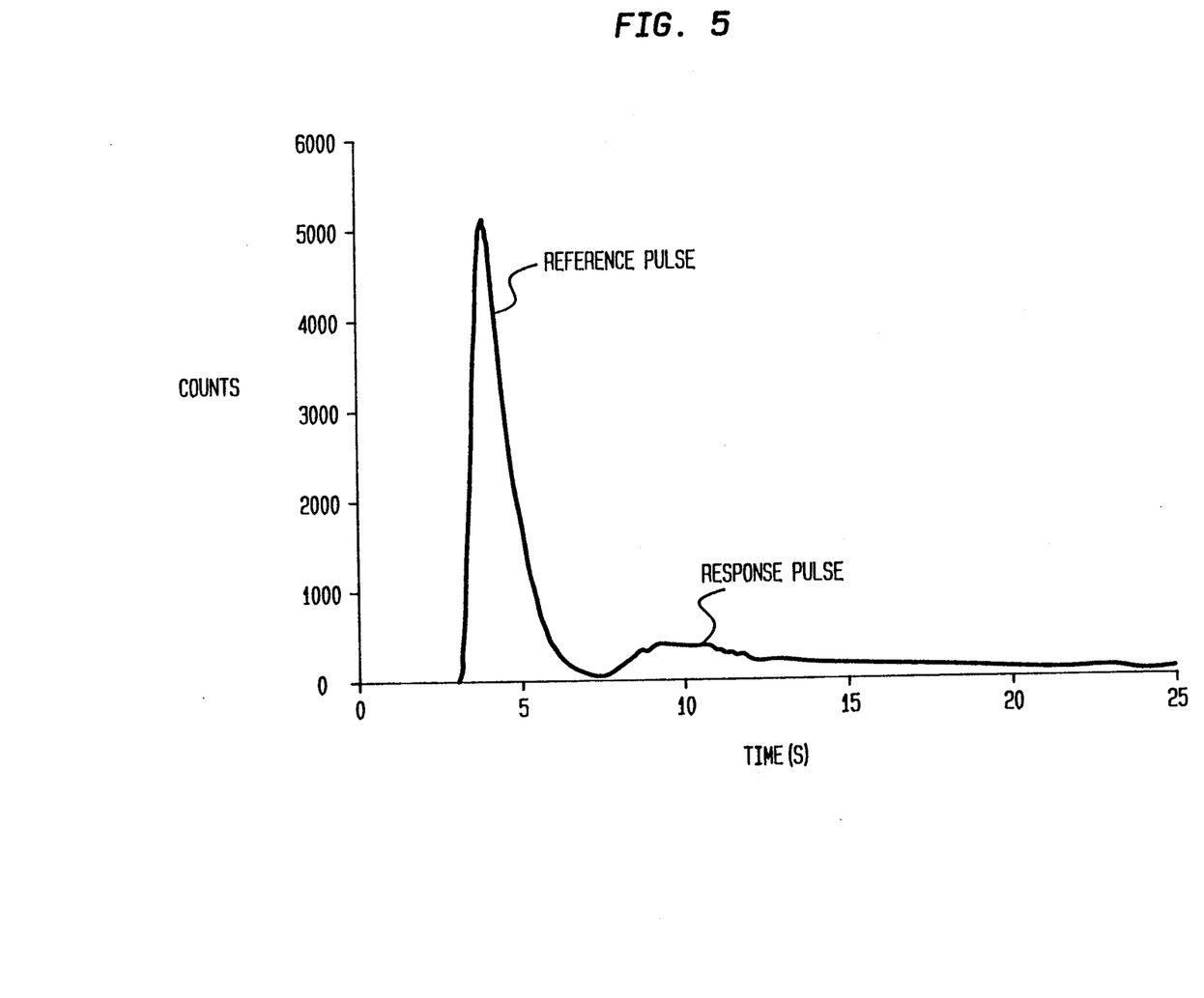
FIG. 5 is a plot of the particle response characteristic of a rotameter.

Such a particle response characteristic plot for a 12.7 cm. long, approximately 9.5 mm. in diameter, electropolished stainless steel sampling tube is reproduced herein as FIG. 4. This plot shows that the sampling tube has a time resolution of approximately a half a second by comparing the widths of the curves representing the reference and response counts of particles at the half heights of such curves. Thus, changes in particle or contaminant count that are taking place at less than a half second will merge to an average and will not be detectable through such a sampling tube. With reference to FIG. 5, the plot of the particle response characteristic of a rotameter is illustrated. This plot shows that a rotameter has such a lagging response that one would not put such a device in a flow circuit through which contaminants are to be measured, such as moisture, because moisture would tend to collect in such a device.

Input and output pulses, after being sensed by particle counters 24 and 26 are acquired by a counter board 30 installed in an expansion slot of a PC 31, or otherwise connected to some other programmable logic computer. Counter board 30 also serves to trigger particle generator 12 and to record the input and output pulses of particles by writing them to files contained within the PC 3. This is accomplished by a program annexed hereto written in MICROSOFT QUICKBASIC that is used to control the operation of counter board 30, preferably a KEITHLEY/METRABYTE CTM-05 counter board, installed in PC 31 which is also provided with a VGA board and monitor. Counter board 30 can be obtained from Keithley/Metrabyte/Asyst/DAC, 440 Myles Standish Blvd., Taunton, Mass. 02780. The computer program is annexed hereto as Appendix A and is covered by a copyright which is owned by the assignee of this application, The BOC Group, Inc. which has no objection to the copying of this computer program, but otherwise reserves all rights herein.

Figure 6:
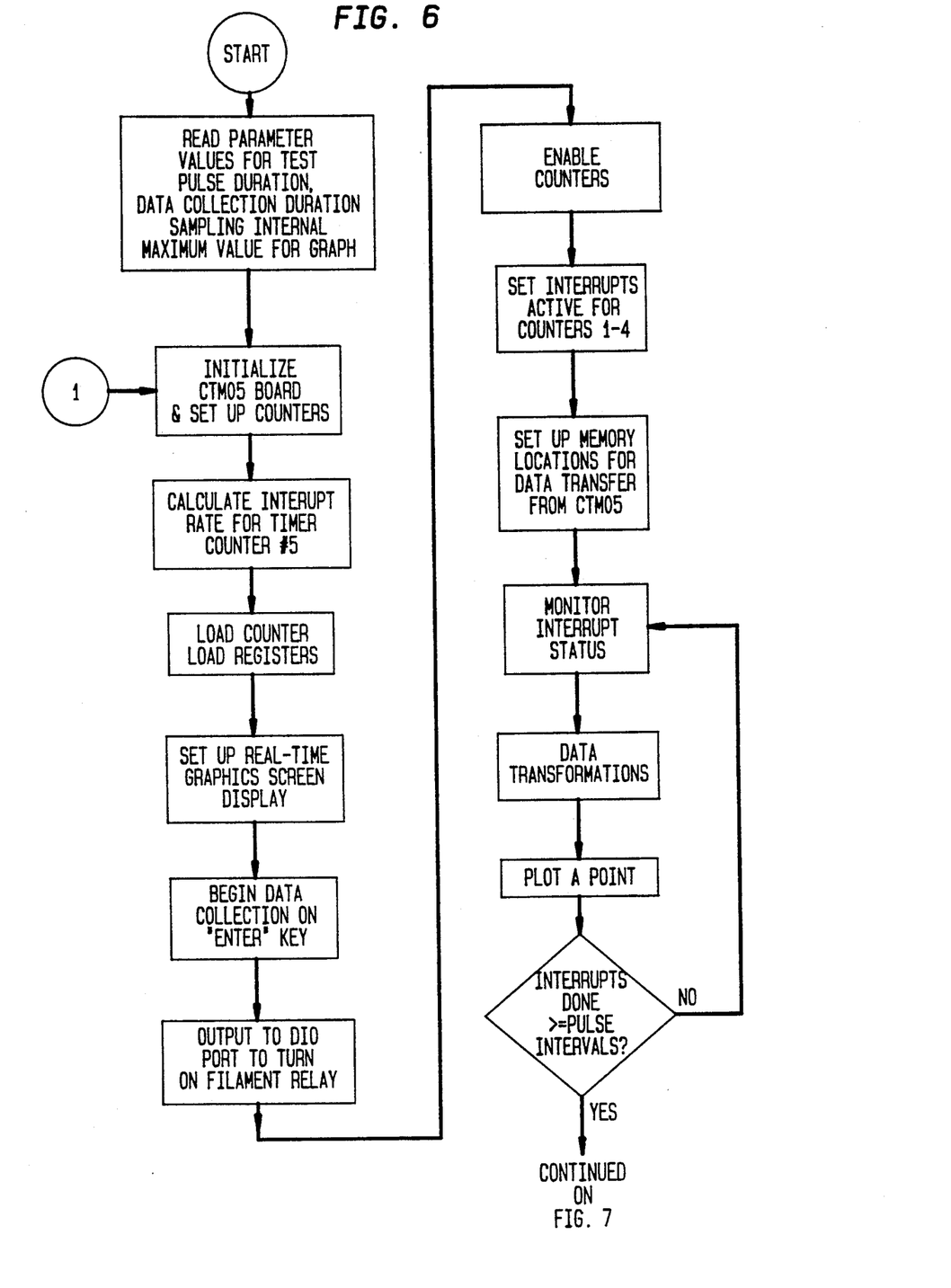
FIGS. 6 and 7 are a flow chart of a computer program that is used to control a Counter/Timer Board installed in a personal computer.
Figure 7:
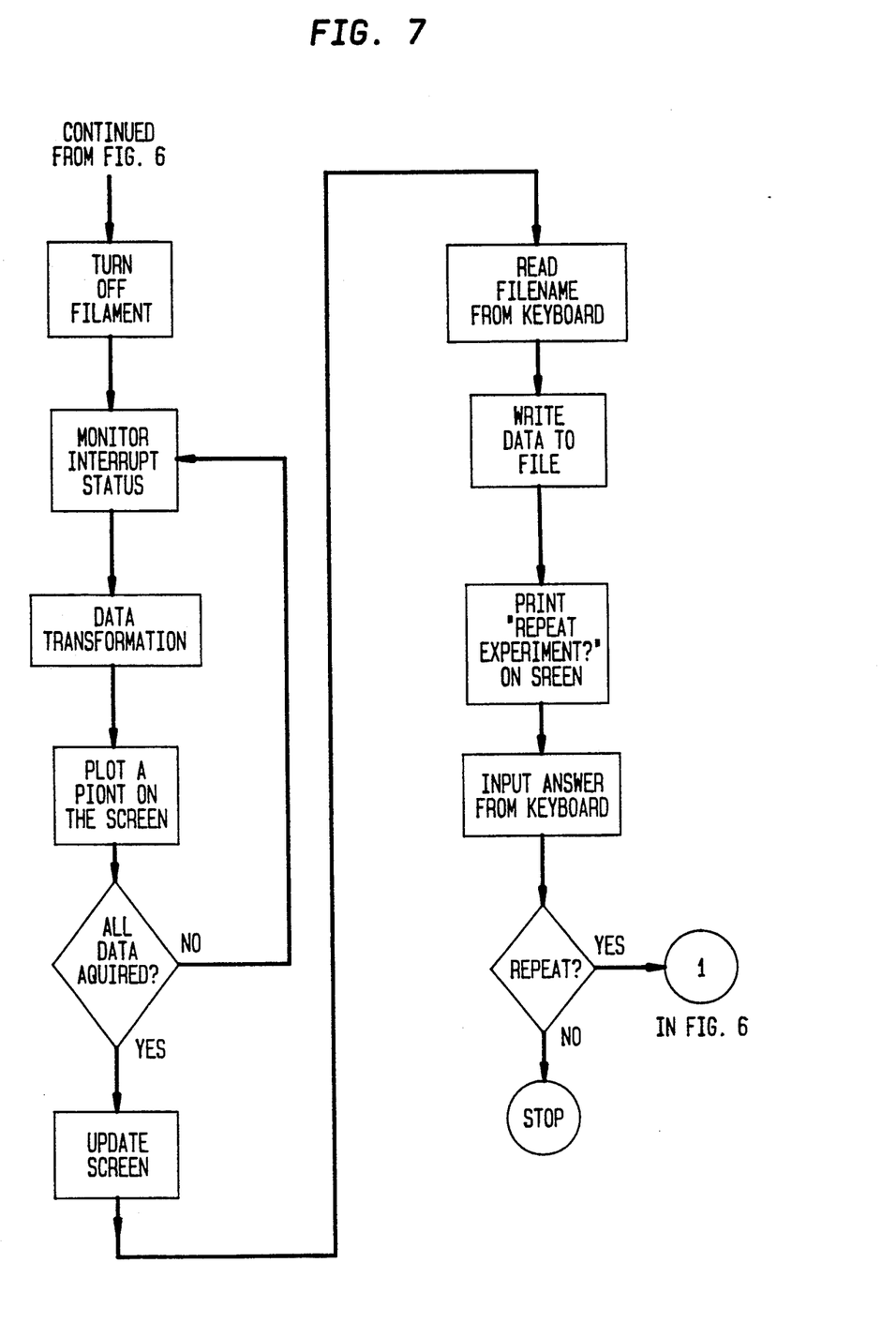

With reference to the flow chart, parameters relating to pulse duration, data collection duration, how long the test is to be run, the sampling interval, the small time intervals in which particles will be sampled, and the maximum value for the graph are inputs supplied by the user of the program. The CTM-05 board will record data and also control particle generator 12. The CTM-05 board is then initialized and the counters are set up. The CTM-05 board has five counters of which the fifth counter is dedicated as an interval timer. The first two counters are cascaded and used to count pulses from condensation nucleus counter 24, and counters 3 and 4 are cascaded and dedicated for counting pulses from the laser particle counter 26.

Thereafter, an interrupt rate is calculated for the fifth counter. From the sampling interval, the number of clock pulses is determined which will set an interrupt for the fifth counter on the CTM-05 board. Additionally, the number of sampling intervals are calculated that are necessary to reach the pulse duration. Thereafter, the registers of the counters are loaded with values of zero, except for the register of the fifth counter which is loaded with a value equal to the number of clock pulses per sampling interval. A real time graphics screen is set up and data collection can begin with pressing the enter key. Any other key aborts the test. Thereafter, an appropriate output is sent to the digital I/O port to turn on the filament. In practice, although not illustrated, power would be applied to particle generator 10 by means of a relay which would be switched by the output to the digital I/O port. The counters are then loaded and enabled. The fifth counter begins to count down the predetermined number of clock pulses. Interrupts are set active for the first four counters and memory locations are set in the PC for data transfer from the CTM-05 counter board. Once the fifth counter is zero, an interrupt triggers a data transfer of each of the counter values from the CTM-05 board to the PC. Counter five then repeats the process of counting down the predetermined number of clock pulses and triggering an interrupt upon reaching zero. Each interrupt triggers a data transfer of the counter's contents to the PC. Simultaneously, interrupt status is monitored by the PC program which determines how many data points have been collected. Data transformations then occur in which the values taken from the PC's memory are transformed to a number of counts. A point is plotted on the graphics display and if the interrupts are not greater than or equal to the pulse intervals, interrupt status is monitored again and this part of the program loops until the interrupts completed are greater than or equal to the pulse intervals. At such time, the filament is turned off. Since there exists a lag between the output pulse and the input pulse, data acquisition must however continue. As such, the monitoring of the interrupt status continues along with data transformation and plotting. The test is completed when it is determined that all data is acquired. When all of the data is acquired, the screen on which the data is plotted is updated. Thereafter, a file name is read from an input to the keyboard of the PC and the data derived from the test is written to the file. After a "repeat experiment message" on screen, the test can be completed again, and in fact, is so completed until a predetermined number of tests are completed that will produce statistically repeatable reference and response curves.

As may be appreciated, a number of files are produced which each contain data points of counts versus time. The computer program could be provided with instructions to signal average these collections of data to produce the reference and response pulses. However, in the instant system, the files are simply output to a spread sheet program which is used to signal average the data. Additionally, each run will produce two sets of data, one for condensation nucleus counter 24 and the other for laser particle counter 26. In practice plots of both sets of data are viewed and the plot showing that the counter was over or underwhelmed is then discarded.

While the invention has been described with reference to a preferred embodiment, it will occur to those skilled in the art that numerous changes, additions and omissions can be made without department from the spirit and scope of the invention.

Appendix A

```
'Particle Pulse Testing Program.

'This program is written in Microsoft QuickBasic (version 4.5).
'It requires a Keithley/Metrabyte CTM-05 counter board
'installed in an IBM-AT compatible computer with a VGA board and
'monitor. The subroutine QBCTM5 is a driver supplied by Keithley
'as a Quickbasic library, QBCTM5.QLB. The CTM-05 board is set
'up such that counters 1 and 2 are cascaded and used to
'count pulses from a CNC. Counters 3 and 4 are cascaded and used
'for counting pulses from a LPC. Counter 5 is set up to provide
'an interrupt at a set time interval and thus acts as a timer.

DIM dio%(9), dat1%(4096), dat2%(4096), dat3%(4096), dat4%(4096)
    DIM dat5%(4096), totalcha&(4096), totalchb&(4096)
    DIM cha&(4096), chb&(4096)
    COMMON SHARED dio%()
    DECLARE SUB qbctm5 (mode%, BYVAL dummy%, flag%)

'get input parameter values
        CLS
        INPUT "Pulse duration (s): "; pulseduration
        INPUT "Data collection duration (s): "; dataduration
        INPUT "Sampling interval (s): "; sampleinterval
        INPUT "Maximum count value for graph: "; maxcounts%
        maxtime% = dataduration initboard:
        'initialize board
        dio%(0) = &H300   'base I/O address for CTM05 board
        dio%(1) = 10      'Fout divider ratio of 10
        dio%(2) = 13      'Fout source = F3 (10kHz) for Fout = 1kHz
        dio%(3) = 0       'compare 2 disabled
        dio%(4) = 0       'compare 1 disabled
        dio%(5) = 0       'time of day disabled
        flag% = 0         'error flag
        mode% = 0         'set master mode register
        CALL qbctm5(mode%, VARPTR(dio%(0)), flag%)
        IF flag% <> 0 THEN PRINT "Error in MODE 0": STOP 'use counter 5 as a timer (interrupt source)
        mode% = 1
        dio%(0) = 5       'counter number
        dio%(1) = 0       'no gating
        dio%(2) = 0       'positive edge trigger
        dio%(3) = 14      'source F4 (1kHz)
        dio%(4) = 0       'disable special gate
        dio%(5) = 0       're-load from load register
        dio%(6) = 1       'count repetitively
        dio%(7) = 0       'binary count
        dio%(8) = 0       'count down
        dio%(9) = 2       'toggle output
        CALL qbctm5(mode%, VARPTR(dio%(0)), flag%)
        IF flag% <> 0 THEN
            PRINT "Error in setting counter 5 configuration"
            STOP
        ENDIF 'set configuration of counters 1 to 4
        dio%(8) = 1       'count up
        dio%(9) = 5       'active low terminal count
        FOR i = 1 TO 4
        dio%(0) = i       'select counter #i
        dio%(3) = i       'clock input source = SRC(Counter #)
        CALL qbctm5(mode%, VARPTR(dio%(0)), flag%)
        IF flag% <> 0 THEN
```

```
        PRINT "Error in setting counter "; i; " configuration"
        STOP
    ENDIF
NEXT i 'determine interrupt rate and load counter 5
Intrate = 1 / sampleinterval
mode% = 3
dio%(0) = 5           'counter 5
DV = 1000! / (Intrate * 2) '1KHz clock/rate with /2 toggle
IF DV < 32768! THEN
dio%(1) = DV
ELSE
dio%(1) = DV - 65536!
ENDIF
IF dio%(1) < 0 THEN
    sr = 1000! / (2 * (dio%(1) + 65536!))
ELSE
    sr = 1000! / (2 * dio%(1))     'actual sampling rate
ENDIF
pulseintervals% = pulseduration * sr
n% = dataduration * sr
CALL qbctm5(mode%, VARPTR(dio%(0)), flag%)
IF flag% <> 0 THEN
    PRINT "Error in loading counter 5 load register"
    STOP
ENDIF 'zero (reset) counters 1 - 4
mode% = 3
dio%(1) = 0        'load data
FOR i = 1 TO 4
dio%(0) = i        'counter number
CALL qbctm5(mode%, VARPTR(dio%(0)), flag%)
IF flag% <> 0 THEN
    PRINT "Error in loading counter "; i; " load register"
    STOP
ENDIF
'setup screen display panel for real-time graphical output
GOSUB screensetup
VIEW PRINT 53 TO 60
oldcounts& = 0: oldi% = 0: PSET (0, 0)

'start data collection
INPUT "Press ENTER to begin (Enter 0 to abort)"; ans$
LOCATE 53, 1: PRINT TAB(70);
IF (ans$ <> "") THEN GOTO getout
VIEW PRINT
LOCATE 49, 26: PRINT " ON "
LOCATE 53, 31: PRINT "DATA ACQUISITION IN PROGRESS"

'output a byte to CTM5 DIO port to turn filament relay on
mode% = 6
dio%(0) = 255  'output byte odd = on, even = off
CALL qbctm5(mode%, VARPTR(dio%(0)), flag%)
IF flag% <> 0 THEN
    PRINT "Error in setting digital output byte"
    STOP
ENDIF 'reset counters 1- 4 and enable counter 5
mode% = 2
dio%(0) = 3              'load and arm
dio%(1) = 1              'select counter 1
dio%(2) = 1              'select counter 2
dio%(3) = 1              'select counter 3
dio%(4) = 1              'select counter 4
dio%(5) = 1              'select counter 5
CALL qbctm5(mode%, VARPTR(dio%(0)), flag%)
IF flag% <> 0 THEN
PRINT "Error in enabling counters"
STOP
ENDIF
```

```
        'set interrupts active for counters 1 - 4
        mode% = 7
        dio%(0) = n%              'number of interrupts
        dio%(1) = -1              'dump segment for counter 1
        dio%(2) = -1              'dump segment for counter 2
        dio%(3) = -1              'dump segment for counter 3
        dio%(4) = -1              'dump segment for counter 4
        dio%(5) = 0               'no dumping of counter 5
        dio%(6) = 0               'no gating by IP0
        dio%(7) = 5               'INTERRUPT LEVEL
        CALL qbctm5(mode%, VARPTR(dio%(0)), flag%)
        IF flag% <> 0 THEN
            PRINT "Error in setting interrupt active"
            STOP
        ENDIF
        'set up mode 11 segments & offsets
        mode% = 11
        dio%(0) = VARPTR(dat1%(0))
        dio%(1) = VARSEG(dat1%(0))
        dio%(2) = VARPTR(dat2%(0))
        dio%(3) = VARSEG(dat2%(0))
        dio%(4) = VARPTR(dat3%(0))
        dio%(5) = VARSEG(dat3%(0))
        dio%(6) = VARPTR(dat4%(0))
        dio%(7) = VARSEG(dat4%(0))
        dio%(8) = VARPTR(dat5%(0))
        dio%(9) = 0                    'disable dumping of counter 5
        CALL qbctm5(mode%, VARPTR(dio%(0)), flag%)
        IF flag <> 0 THEN
            PRINT "error in mode 11 dump addresses"
            STOP
        ENDIF 'count interrupts to time filament pulse duration
        mode% = 8 timepulse:
        CALL qbctm5(mode%, VARPTR(dio%(0)), flag%)
        j% = dio%(1) - 1
        IF j% > 0 THEN GOSUB plotapoint    'plot a point
                                           'wait for end of pulse
        IF (pulseintervals% > dio%(1)) THEN GOTO timepulse 'turn off filament
        mode% = 6
        dio%(0) = 0
        CALL qbctm5(mode%, VARPTR(dio%(0)), flag%)
        LOCATE 49, 26: PRINT " OFF"

'monitor interrupt for completion of data acquisition
        mode% = 8 checkint:
        CALL qbctm5(mode%, VARPTR(dio%(0)), flag%)
        j% = dio%(1) - 1: IF (j% > 0) THEN GOSUB plotapoint
        IF dio%(0) = 0 THEN GOTO dataready
        GOTO checkint dataready:
        LOCATE 47, 30: PRINT "  0.0"
        LOCATE 53, 31: PRINT "DATA ACQUISITION COMPLETED         "
        LOCATE 55, 1
        INPUT "Filename for data:"; afile$
        OPEN afile$ FOR OUTPUT AS #1
        image$ = "####    ###.#####    #########    #########"
        FOR i% = 0 TO n% - 1
        time = i% / sr
        PRINT #1, USING image$;i;time;cha&(i%);chb&(i%)
        NEXT i%
        CLOSE #1 repeatexpt:
        LOCATE 55, 1
        INPUT "Repeat experiment with current parameters"; ans$
```

```
        LOCATE 55, 1
        PRINT "                                                    "
        IF ans$ = "y" OR ans$ = "Y" THEN GOTO initboard
        IF ans$ = "n" OR ans$ = "N" THEN GOTO getout
        GOTO repeatexpt screensetup:
        SCREEN 12
        COLOR 7
        VIEW PRINT
        WIDTH 80, 60
        VIEW (50, 1)-(638, 318), 7, 15
        WINDOW (1, 0)-(n%, maxcounts%)
        LOCATE 1, 1: PRINT USING "#####"; maxcounts%
        LOCATE 40, 5: PRINT "0"
        LOCATE 42, 7: PRINT "0"
        LOCATE 42, 40: PRINT "TIME (s)"
        LOCATE 42, 76: PRINT USING "#####"; maxtime%
        LOCATE 47, 15
        PRINT USING "TIME REMAINING ##### s"; maxtime%
        LOCATE 49, 15: PRINT "FILAMENT IS OFF"
        LOCATE 47, 54
        PRINT USING "PULSE DURATION ##.# s"; pulseduration
        LOCATE 49, 49
        PRINT USING "SAMPLING INTERVAL ###.## s"; 1 / sr
        LOCATE 44, 10
        COLOR 9: PRINT "CHANNEL A (CNC) =            0"
        LOCATE 44, 50
        COLOR 4
        PRINT "CHANNEL B (LPC) =            0"
        COLOR 7
        RETURN plotapoint:
        'plot a point on the screen
        IF j% = oldj% THEN track& = track& + 1: RETURN
        IF dat1%(j%) < 0 THEN
            A& = 65536! + dat1%(j%)
        ELSE
            A& = dat1%(j%)
        ENDIF
        IF dat2%(j%) < 0 THEN
            b& = 65536! + dat2%(j%)
        ELSE
            b& = dat2%(j%)
        ENDIF
        IF dat3%(j%) < 0 THEN
            c& = 65536! + dat3%(j%)
        ELSE
            c& = dat3%(j%)
        ENDIF
        IF dat4%(j%) < 0 THEN
            d& = 65536! + dat4%(j%)
        ELSE
            d& = dat4%(j%)
        ENDIF
        totalcha&(j%) = A& + b& * 65536!
        LOCATE 44, 29: COLOR 9
        PRINT USING "########"; totalcha&(j%)
        totalchb&(j%) = c& + d& * 65536!
        LOCATE 44, 69: COLOR 4
        PRINT USING "########"; totalchb&(j%): COLOR 7
        k% = j% - 1
        cha&(j%) = totalcha&(j%) - totalcha&(k%)
        chb&(j%) = totalchb&(j%) - totalchb&(k%)
        oldj% = j%
        olda& = cha&(k%): oldb& = chb&(k%)
        LINE (k%, olda&)-(j%, cha&(j%)), 9
        LINE (k%, oldb&)-(j%, chb&(j%)), 4
        timeleft = dataduration - j% / sr
        LOCATE 47, 30: PRINT USING "###.#"; timeleft
        RETURN getout:
        END
```

I claim:

1. A method of determining a particle response characteristic of a device, said method comprising the steps of:
   (a) introducing an input pulse of particles into a flowing fluid;
   (b) introducing the flowing fluid into the device after the introduction of the input pulse of particles so that an output pulse of particles is present in the fluid after the fluid has passed through the device;
   (c) measuring an input count of particles produced by the input pulse of particles on a particle count versus time basis;
   (d) recording the input count of particles;
   (e) measuring an output count of particles produced by the output pulse of particles on the particle count versus time basis;
   (f) recording the output count of particles;
   (g) repeating steps (a), (b), (c), (d), (e) and (f) such that a sufficient number of input and output counts of particles are produced that signal averaging of the input and output counts of particles produces statistically repeatable reference and response counts of particles, respectively, on the particle count versus time basis; and
   (f) determining the reference and response counts of the particles from the recorded input and output counts of particles by signal averaging the input and output counts of particles, whereby a comparison between the reference and response counts of particles is the particle response characteristic of the device.

2. The method of claim 1, wherein the fluid comprises a gas stream and each of the input pulses are introduced into the gas stream by electrically energizing a filament located within the gas stream for a preselected time interval.

3. The method of claim 2, wherein input and output counts of particles are measured by a condensation nucleus counter or a laser particle counter depending upon particle count within the input and output pulses.

4. The method of claim 3, wherein steps (a), (b), (c), (d), (e) and (f) are repeated by first repeating steps (a), (c) and (d) so that the input counts of particles are measured and recorded without passing the flowing fluid through the device and then repeating steps (a), (b), (e) and (f) so that the flowing fluid is passed through the device and the output counts of the particles are recorded.

5. The method of claim 4, wherein the flowing fluid is a gas mixture comprising nitrogen and oxygen.

6. The method of claim 4, wherein the input pulse of particles is introduced into the flowing fluid by locating an electrical filament within the flowing fluid and energizing the electrical filament with electric current pulses to create the input pulses of particles.

7. The method of claim 6, wherein:
   the flowing fluid comprises nitrogen;
   the electrical filament is fabricated of Tungsten; and
   the particles comprise nitrides of the Tungsten.

8. The method of claim 1, wherein input and output counts of particles are measured by a condensation nucleus counter or a laser particle counter depending upon particle count within the input and output pulses.

9. The method of claim 1, wherein steps (a), (b), (c), (d), (e) and (f) are repeated by first repeating steps (a), (c) and (d) so that the input counts of particles are measured and recorded without passing the flowing fluid through the device and then repeating steps (a), (b), (e) and (f) so that the flowing fluid is passed through the device and the output counts of particles are recorded.

10. The method of claim 1, wherein the input pulse of particles is introduced into the flowing fluid by locating an electrical filament within the flowing fluid and energizing the electrical filament with electric current pulses to create the input pulses of particles.

11. The method of claim 10, wherein:
    the flowing fluid comprises nitrogen;
    the electrical filament is fabricated of Tungsten; and
    the particles comprise nitrides of the Tungsten.

* * * * *

UNITED STATES PATENT AND TRADEMARK OFFICE
CERTIFICATE OF CORRECTION

PATENT NO. : 5,255,555
DATED : October 26, 1993
INVENTOR(S) : Kevin McKeigue It is certified that error appears in the above—identified patent and that said Letters Patent is hereby corrected as shown below:

Col. 15, line 25, delete "(f)" and substitute --(h)--.

Signed and Sealed this

Twelfth Day of April, 1994

Attest:

BRUCE LEHMAN

*Attesting Officer*     *Commissioner of Patents and Trademarks*